(12) United States Patent  
Lischinsky

(10) Patent No.: US 11,660,449 B2  
(45) Date of Patent: May 30, 2023

(54) ARTIFICIAL INTELLIGENCE FOR IMPROVED SKIN TIGHTENING

(71) Applicant: AIGAIN BEAUTY LTD., Haifa (IL)

(72) Inventor: Daniel Eduardo Lischinsky, Ramat Yishay (IL)

(73) Assignee: AIGAIN BEAUTY LTD., Haifa (IL)

( * ) Notice: Subject to any disclaimer, the term of this patent is extended or adjusted under 35 U.S.C. 154(b) by 87 days.

(21) Appl. No.: 15/733,911

(22) PCT Filed: Jun. 10, 2019

(86) PCT No.: PCT/IB2019/054797  
§ 371 (c)(1),  
(2) Date: Dec. 1, 2020

(87) PCT Pub. No.: WO2019/239275  
PCT Pub. Date: Dec. 19, 2019

(65) Prior Publication Data  
US 2021/0290953 A1 Sep. 23, 2021

Related U.S. Application Data

(60) Provisional application No. 62/683,070, filed on Jun. 11, 2018.

(51) Int. Cl.  
*A61N 1/32* (2006.01)  
*G16H 20/30* (2018.01)  
*A61N 1/40* (2006.01)

(52) U.S. Cl.  
CPC .............. *A61N 1/328* (2013.01); *A61N 1/40* (2013.01); *G16H 20/30* (2018.01)

(58) Field of Classification Search  
CPC .................................. A61N 1/328; A61N 1/40  
See application file for complete search history.

(56) References Cited

U.S. PATENT DOCUMENTS 5,919,219 A 7/1999 Knowlton  
6,405,090 B1 6/2002 Knowlton  
(Continued)

FOREIGN PATENT DOCUMENTS

CN 107530544 A 2/2018  
CN 107735039 A 2/2018  
(Continued)

OTHER PUBLICATIONS

IN Application # 202047051273 Office Action dated Dec. 1, 2021.  
(Continued)

*Primary Examiner* — Allen Porter  
*Assistant Examiner* — Adreanne A. Arnold  
(74) *Attorney, Agent, or Firm* — Kligler & Associates Patent Attorneys Ltd

(57) ABSTRACT

A system (20) includes a plurality of electrodes (28), one or more radiofrequency (RF) generators (30), and a controller (36). The controller is configured to treat skin of a user (22), using one or more decision rules, responsively to multiple ascertained values of at least one parameter, by iteratively ascertaining at least one respective value of the ascertained values, by applying at least one of the decision rules to the ascertained value, identifying a treatment setting from among multiple treatment settings, and causing the RF generators to cause one or more RF currents to pass, through the skin, between at least some of the electrodes in accordance with the identified treatment setting. The controller is further configured to modify at least one of the decision rules in response to the ascertained values. Other embodiments are also described.

51 Claims, 5 Drawing Sheets

(56) References Cited

U.S. PATENT DOCUMENTS

| | | |
|---|---|---|
| 6,413,255 B1 | 7/2002 | Stern |
| 6,453,202 B1 | 9/2002 | Knowlton |
| 6,889,090 B2 | 5/2005 | Kreindel |
| 7,041,100 B2 | 5/2006 | Kreindel |
| 7,141,049 B2 | 11/2006 | Stern et al. |
| 7,238,183 B2 | 7/2007 | Kreindel |
| 7,957,815 B2 | 6/2011 | Wyeth et al. |
| 8,206,381 B2 | 6/2012 | Lischinsky et al. |
| 8,221,410 B2 | 7/2012 | Knowlton et al. |
| 8,357,150 B2 | 1/2013 | Adanny et al. |
| 8,512,331 B2 | 8/2013 | Lischinsky et al. |
| 8,603,088 B2 | 12/2013 | Stern et al. |
| 8,606,366 B2 | 12/2013 | Flyash et al. |
| 8,700,176 B2 | 4/2014 | Azar et al. |
| 8,728,071 B2 | 5/2014 | Lischinsky et al. |
| 9,028,480 B2 | 5/2015 | Adanny et al. |
| 9,072,882 B2 | 7/2015 | Adanny et al. |
| 9,227,081 B2 | 1/2016 | Adanny et al. |
| 9,636,175 B2 | 5/2017 | Stern et al. |
| 9,827,437 B2 | 11/2017 | Lischinsky et al. |
| 9,844,682 B2 | 12/2017 | Lischinsky et al. |
| 9,962,220 B2 | 5/2018 | Domankevitz |
| 2005/0119714 A1 | 6/2005 | Sieracki et al. |
| 2005/0278002 A1* | 12/2005 | Eimerl ............ A61B 18/203 607/88 |
| 2008/0183251 A1* | 7/2008 | Azar ............ A61B 18/14 607/101 |
| 2010/0036378 A1 | 2/2010 | Savery et al. |

FOREIGN PATENT DOCUMENTS

| | | | |
|---|---|---|---|
| DE | 202017107092 U1 | 2/2018 | |
| EP | 2469699 A2 * | 6/2012 | ......... A61B 18/1206 |
| EP | 2469699 A2 | 6/2012 | |
| JP | S6088948 U | 6/1985 | |
| JP | 2004129866 A | 4/2004 | |
| WO | 2007146213 A2 | 12/2007 | |
| WO | 2012023129 A1 | 2/2012 | |
| WO | 2013071307 A1 | 5/2013 | |
| WO | 2014009875 A2 | 1/2014 | |
| WO | 2015068621 A1 | 5/2015 | |
| WO | WO-2016162234 A1 * | 10/2016 | ............... A61N 1/06 |

OTHER PUBLICATIONS

AU Application # 2019286380 Office Action dated Aug. 19, 2021.
EP Application # 19820339.0 Search Report dated Feb. 17, 2022.
AU Application # 2019286380 Office Action dated Jan. 31, 2022.
Elman et al., "Non-invasive therapy of wrinkles and lax skin using a novel multisource phase-controlled radio frequency system," Journal of Cosmetic and Laser Therapy, vol. 12, pp. 81-86, Apr. 2010.
International Application # PCT/IB2019/054797 Search Report dated Oct. 7, 2019.
RU Application # 2020136902 Office Action dated Aug. 5, 2022.
JP Application # 2020567834 Office Action dated Feb. 21, 2023.

* cited by examiner

| DOMAIN | CV | PHASE - 28a | PHASE - 28b | PHASE - 28c | PHASE - 28d |
|---|---|---|---|---|---|
| [x0, x1] | y1 | 0 | 180 | 0 | INACTIVE |
| [x1, x2] | y2 | 0 | INACTIVE | 180 | 0 |
| [x2, x3] | y3 | INACTIVE | 180 | INACTIVE | 0 |
| [x3, x4] | y4 | 0 | 180 | 0 | 180 |
| [x4, x5] | y5 | 0 | 180 | 180 | 0 |

ARTIFICIAL INTELLIGENCE FOR IMPROVED SKIN TIGHTENING

CROSS-REFERENCE TO RELATED APPLICATIONS

The present application claims the benefit of U.S. Provisional Appl. No. 62/683,070, entitled "Constant RF energy density for skin tightening—therapeutic method and apparatus," filed Jun. 11, 2018, whose disclosure is incorporated herein by reference.

FIELD OF THE INVENTION

The present invention relates generally to the field of cosmetics, and particularly to the treatment of skin.

BACKGROUND

U.S. Pat. No. 8,700,176 describes skin treating devices and systems for delivering radiofrequency (RF) electromagnetic energy to the skin. The devices include one or more electromagnetic RF generating units, multiple RF electrode groups and a controller for controllably applying RF energy to the skin through any selected RF electrode group or any selected RF electrode group combination selected from the multiple groups. The electrodes may be stationary and/or movable electrodes. Different RF frequencies and/or frequency bands may be used.

SUMMARY OF THE INVENTION

There is provided, in accordance with some embodiments of the present invention, a system including a plurality of electrodes, one or more radiofrequency (RF) generators, and a controller. The controller is configured to treat skin of a user, using one or more decision rules, responsively to multiple ascertained values of at least one parameter, by iteratively ascertaining at least one respective value of the ascertained values, by applying at least one of the decision rules to the ascertained value, identifying a treatment setting from among multiple treatment settings, and causing the RF generators to cause one or more RF currents to pass, through the skin, between at least some of the electrodes in accordance with the identified treatment setting. The controller is further configured to modify at least one of the decision rules in response to the ascertained values.

In some embodiments, the controller is configured to modify the at least one of the decision rules using artificial intelligence.

In some embodiments, a different respective one of the RF generators is connected to each one of the electrodes.

In some embodiments,
the electrodes include at least three electrodes, at least one pair of the electrodes being spaced farther apart from one another than is another pair of the electrodes,
the treatment settings specify respective groups of the electrodes for activation, and
the controller is configured to cause the RF generators to cause the RF currents to pass between the group of the electrodes specified, for activation, by the identified treatment setting.

In some embodiments, at least some of the treatment settings specify, for activation, different respective ones of the groups.

In some embodiments,
the treatment settings further specify respective sets of phases, at least some of the treatment settings specifying different respective ones of the sets for the same one of the groups, and
the controller is configured to cause the RF generators to cause the RF currents to pass between the group of the electrodes by causing the RF generators to apply respective RF signals to the group of the electrodes, the RF signals having, respectively, the set of phases specified by the identified treatment setting.

In some embodiments, the system further includes a surface shaped to define a track,
at least one of the electrodes is moveable along the track,
at least some of the treatment settings specify different respective inter-electrode separations, and
the controller is configured to cause the RF generators to cause the RF currents to pass between the at least some of the electrodes in accordance with the identified treatment setting by:
  moving the moveable electrode along the track such that the moveable electrode and another one of the electrodes are spaced apart from one another by the inter-electrode separation specified by the identified treatment setting, and
  subsequently to moving the moveable electrode, causing the RF generators to cause the RF currents to pass between the moveable electrode and the other one of the electrodes.

In some embodiments,
the decision rules are represented by a mapping from multiple domains of the parameter to the treatment settings, respectively,
the controller is configured to identify the treatment setting by identifying the domain to which the ascertained value belongs, and
the controller is configured to modify the at least one of the decision rules by modifying at least one boundary of at least one of the domains.

In some embodiments,
the domains are associated with different respective characteristic values, and
the controller is configured to modify the boundary of the at least one of the domains by:
  modifying the characteristic value of the at least one of the domains, based on those of the ascertained values belonging to the at least one of the domains, and
  setting the boundary responsively to the modified characteristic value of the at least one of the domains.

In some embodiments, the controller is configured to set the boundary to be equidistant from (i) the modified characteristic value of the at least one of the domains, and (ii) the characteristic value of another one of the domains that is adjacent to the at least one of the domains.

In some embodiments, the controller is configured to modify the characteristic value of the at least one of the domains by:
  computing a mean of those of the ascertained values belonging to the at least one of the domains, and
  setting the characteristic value to a weighted average of (i) the characteristic value, and (ii) the mean.

In some embodiments,
the ascertained values are first ascertained values, and
the domains include multiple skin-area domains corresponding to respective skin areas,
  each of the skin-area domains corresponding to a respective one of the skin areas by virtue of having been defined based on second ascertained values of the parameter associated with the skin area.

In some embodiments, the skin areas include a cheek and a forehead.

In some embodiments, the domains further include one or more improper-electrical-contact domains corresponding to different respective states in which the electrodes are not in proper electrical contact with the skin, and the controller is further configured to:

ascertain another value of the parameter, ascertain that the other value belongs to one of the improper-electrical-contact domains, and cease treating the skin, responsively to ascertaining that the other value belongs to the improper-electrical-contact domain.

In some embodiments, the states include a state in which the electrodes are not in any electrical contact with the skin.

In some embodiments, the states include a state in which the electrodes are in electrical contact with the skin but not via a layer of gel having a thickness within a predefined range.

In some embodiments, the controller is further configured to generate an output indicating the state to which the improper-electrical-contact domain corresponds.

In some embodiments, the system further includes a temperature sensor configured to measure a temperature of the skin and to generate a temperature-sensor output responsively thereto, the ascertained values include temperature-values of the temperature, and the controller is configured to ascertain the temperature-values responsively to the temperature-sensor output.

In some embodiments, the system further includes an electric-current sensor configured to measure at least some of the RF currents and to generate an output responsively thereto, and the controller is configured to ascertain the ascertained values responsively to the output.

In some embodiments, the ascertained values include electric-current-property-values of a property of the at least some of the RF currents.

In some embodiments, the system further includes a voltage sensor configured to measure a voltage associated with at least some of the RF currents and to generate a voltage-sensor output responsively thereto, and the controller is configured to ascertain the ascertained values responsively to the voltage-sensor output.

In some embodiments, the ascertained values include voltage-property-values of a property of the voltage.

In some embodiments, the ascertained values include impedance-values of an impedance of the skin.

In some embodiments, the controller is further configured to cause the RF generators, prior to treating the skin, to cause a pre-treatment electric current to pass, through the skin, between any pair of the electrodes, and the controller is configured to ascertain an initial one of the ascertained values based on the pre-treatment electric current.

In some embodiments, the system further includes a server configured to communicate with the controller over a computer network, and the server and the controller are configured to cooperatively carry out a process that includes:

comparing a quantity derived from the ascertained values to a baseline quantity, and responsively to the comparing, generating an output to the user.

In some embodiments, the output includes a message indicating an attribute of the skin.

In some embodiments, the output includes a recommendation for a skin-care product.

There is further provided, in accordance with some embodiments of the present invention, a method including, using one or more decision rules, treating skin of a user responsively to multiple ascertained values of at least one parameter, by iteratively ascertaining at least one respective value of the ascertained values, by applying at least one of the decision rules to the ascertained value, identifying a treatment setting from among multiple treatment settings, and causing one or more radiofrequency (RF) currents to pass, through the skin, between at least some of a plurality of electrodes in accordance with the identified treatment setting. The method further includes modifying at least one of the decision rules in response to the ascertained values.

The present invention will be more fully understood from the following detailed description of embodiments thereof, taken together with the drawings, in which:

DETAILED DESCRIPTION OF EMBODIMENTS

Overview

Figure 1:
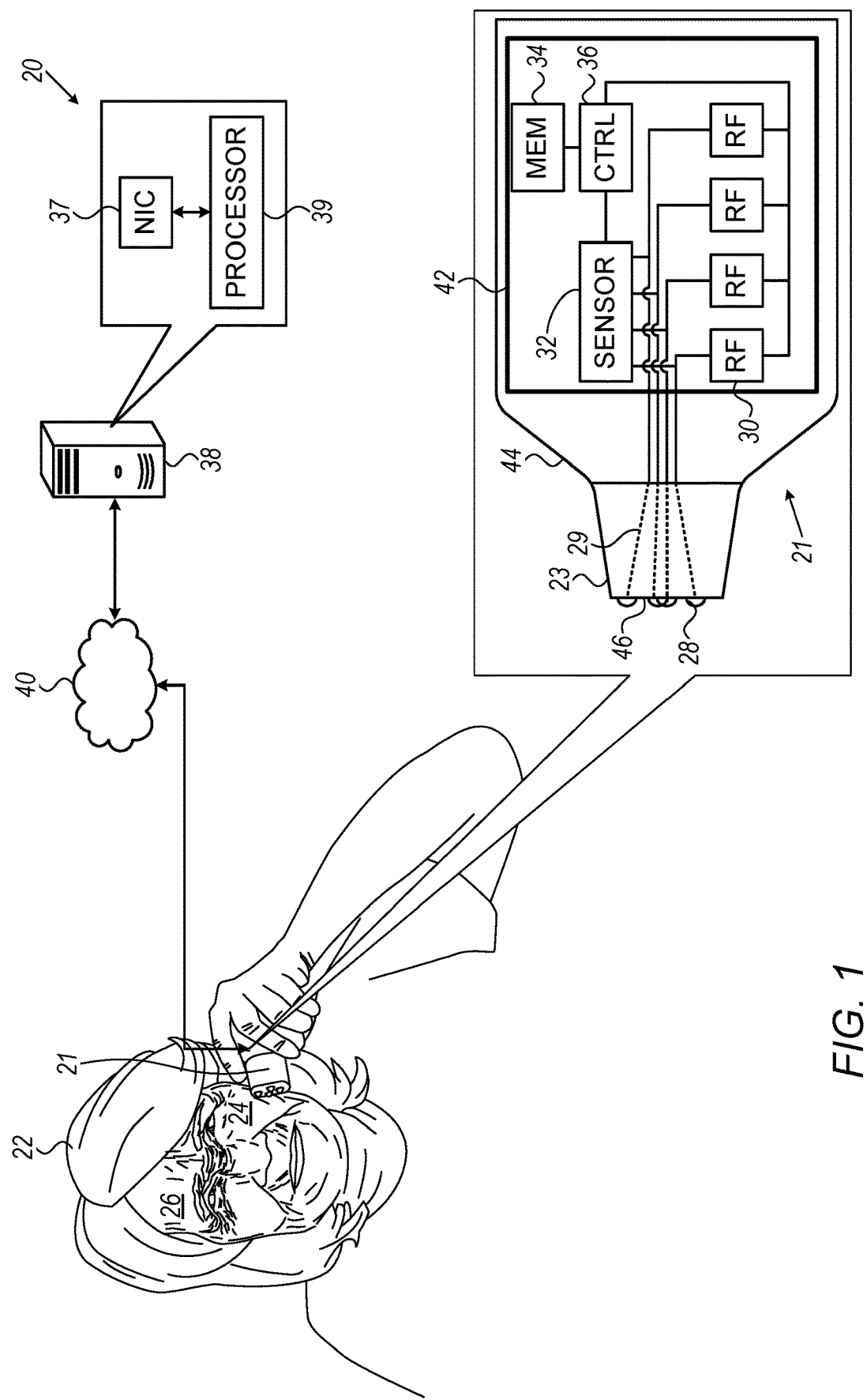
FIG. 1 is a schematic illustration of a system for treating skin of a user, in accordance with some embodiments of the present invention.

When the dermis layer of skin is heated to around 50-52° C., the collagen fibers in the dermis remodel, thus causing the skin to become tightened. Hence, some skin-tightening techniques involve heating the skin by applying RF energy to the skin. The RF energy may be applied, for example, using a handheld treatment head comprising a pair of electrodes. In particular, RF currents may be passed between the pair of electrodes while the electrodes are in electrical contact with the skin, such that the RF currents penetrate the skin.

In general, the depth to which each RF current penetrates is an increasing function of the distance between the electrodes. For example, the penetration depth for a pair of cylindrical electrodes may be approximately half the distance between the pair. Hence, a challenge, when using the same RF device to tighten multiple areas of skin, is that the depth of the skin that is to be treated—and hence the desired penetration depth of the RF currents—may vary from one area to the next. For example, while the deepest portion of the dermis in the cheek or chin may be between 0.2 and 3 mm from the surface of the skin, the dermis in the forehead may be no deeper than between 0.1 and 1 mm. Thus, a penetration depth that is appropriate for the cheek may be dangerous for the forehead, while a penetration depth appropriate for the forehead may be ineffective for the cheek.

To overcome this challenge, the inter-electrode distance (or "separation") may be varied in accordance with the depth of the skin. For example, a first pair of electrodes at a larger distance from one another may be used to treat the cheek, while a second pair of electrodes at a smaller distance from one another may be used to treat the forehead. Alternatively, the distance between a single pair of electrodes may be adjusted in accordance with the depth of the skin, by moving one or both of the electrodes.

The above approach necessitates measuring the depth of the skin during the treatment session, or at least measuring a parameter that is indicative of the depth. One such parameter is the impedance of the skin; hence, in theory, the electrodes may be used to measure the impedance of the skin, and the inter-electrode separation may be varied in accordance with the measured impedance. However, the impedance of any given area of skin in one user may be different from that of the same area of skin in a different user. Moreover, even in a single user, the impedance of any given area of skin may vary over time.

To address this challenge, in embodiments of the present invention, the handheld treatment device comprises a controller, configured to apply the RF currents in accordance with particular user-specific decision rules, and to continually update the decision rules over time, using artificial intelligence. In particular, during the treatment session, the controller repeatedly ascertains the value of a parameter, such as the impedance of the user's skin. Based on each ascertained value, the controller, using the decision rules, identifies the appropriate treatment setting—including, for example, the appropriate inter-electrode separation—and then applies one or more RF currents in accordance with the identified treatment setting. Following the treatment session, the controller may revise the decision rules, based on the ascertained parameter values.

For example, for each user, multiple domains of impedance values may be mapped to different respective treatment settings corresponding to different respective areas of skin, each pair of adjacent domains bordering one another at a respective decision boundary. Thus, for example, for one particular hypothetical user, impedances less than 350Ω may be mapped to a treatment setting appropriate for the forehead, while impedances greater than 350Ω may be mapped to another treatment setting appropriate for the cheek. During the treatment session, the controller may identify the domain to which each ascertained impedance value belongs, and then select the treatment setting to which the domain is mapped. Subsequently to the treatment session, the controller may modify at least one of the decision boundaries, based on the ascertained impedance values.

In some embodiments, to modify the decision boundaries, the controller first updates the "characteristic impedance" $Z^c$ of each of the skin areas that was treated, based on the impedance values for the skin area that were ascertained during the treatment session. In response to the updated characteristic impedances, the controller may set each decision boundary to be equidistant from the respective characteristic impedances of the two skin areas that meet at the decision boundary.

In some embodiments, to update $Z^c$, the controller first computes the average $Z^a$ of the impedance values that were acquired while the skin area was treated. Subsequently, the controller computes a weighted average of the current characteristic impedance and $Z^a$, i.e., the controller sets the new characteristic impedance, $Z^c(n)$, equal to $\alpha*Z^c(n-1)+(1-\alpha)*Z^a(n)$, where a is, for example, between 0.3 and 0.99, e.g., between 0.85 and 0.95. (In some embodiments, the controller does not update $Z^c$ unless the skin area was treated for at least a predefined minimum duration, such as one minute, and/or unless a predefined minimum number of impedance values for the skin area were acquired.)

Typically, upon the user activating the treatment device, the controller obtains an initial impedance measurement by applying a short RF current, referred to herein as a "prepulse," to the skin. Based on this initial measurement, the controller selects the appropriate treatment setting, and begins the treatment in accordance with this setting. Subsequently, as the regular treatment pulses are applied, the impedance is measured periodically, e.g., with a period of between 0.1 and 1 seconds. Based on each periodic measurement, the controller decides whether to use a different treatment setting.

Typically, the controller is further configured to identify situations in which the electrodes lack proper electrical contact with the skin, such as where the treatment device was lifted from the skin during the treatment session. In response thereto, the controller may pause or stop the treatment session.

Typically, the impedance of the skin depends on the amount of moisture in the skin. Hence, in some embodiments, the controller, or a cloud-based server, may identify that the skin of the user is dry, based on the impedance values of the skin that were ascertained during the treatment session. For example, the controller or server may compare the current characteristic impedance for a particular skin area to a baseline characteristic impedance for the same user, and/or to a baseline characteristic impedance of a group of other users. If the current characteristic impedance deviates from the baseline, a message recommending use of a moisturizer may be sent to the user.

System Description

Reference is initially made to FIG. 1, which is a schematic illustration of a system 20 for treating skin of a user 22, in accordance with some embodiments of the present invention. In general, system 20 may be used to treat any suitable area of skin, such as skin of a cheek 24, a forehead 26, another portion of the face, an arm, a leg, or an abdomen.

System 20 comprises a handheld skin-tightening device 21, which may be made from plastic and/or any other suitable material. Device 21 comprises a shell (or "case") 44 coupled to a treatment head 23. Treatment head 23, which is further described below with reference to FIG. 2, comprises a plurality of electrodes 28. Electrodes 28 are typically disposed on a distal surface 46 of the treatment head or within apertures in distal surface 46, e.g., such that the electrodes protrude from distal surface 46.

Shell 44 contains one or more RF generators 30 connected to electrodes 28, typically via wires 29 passing between shell 44 and treatment head 23. Typically, shell 44 further contains a controller (CTRL) 36, a memory 34, and a sensor 32. Typically, RF generators 30, controller 36, memory 34, and sensor 32, along with any one or more of the additional components described below, are mounted on an electronic circuit board 42. In some embodiments, two or more of these components are integrated into a single chip. For example, device 21 may comprise a chip comprising both controller 36 and memory 34, such as the CY8C4247LQI-BL473 chip manufactured by Cypress Semiconductor™. In some embodiments, memory 34 comprises both an internal memory, which is integrated with controller 36 as described above, and an external memory chip.

Typically, controller 36 is configured to perform at least some of the functionality described herein by executing firmware and/or software code. Alternatively, the functionality of controller 36 may be implemented entirely in hardware.

To use device 21, user 22 first covers distal surface 46 (or at least electrodes 28) with a layer of gel having a thickness within a predefined range, such as 2-70 mm. Subsequently, the user runs treatment head 23 over the user's skin such that electrodes 28 are in electrical contact with the skin via the gel. As the treatment head is run over the skin, controller 36 treats the skin of user 22 with one or more RF electric currents, by causing the RF generators to pass the currents through the skin between the electrodes in accordance with feedback from sensor 32 and data from memory 34.

More specifically, during and/or immediately after the application of at least some of the electric currents, sensor 32 measures a relevant characteristic of the skin or of the electric current, and generates an output signal to controller 36 responsively thereto. For example, sensor 32 may comprise a temperature sensor, configured to measure the temperature of the skin during and/or immediately after the application of the electric current. (In general, an electric current passed through thinner skin causes a greater increase in temperature, relative to an electric current passed through thicker skin.) Alternatively or additionally, sensor 32 may comprise a current sensor, configured to measure the electric current applied to the skin. Alternatively or additionally, sensor 32 may comprise a voltage sensor, configured to measure a voltage associated with the electric current, such as the voltage at one or more of the activated electrodes, as the current is applied. Alternatively or additionally, sensor 32 may comprise a moisture sensor, configured to measure the moistness of the skin. Alternatively or additionally, sensor 32 may comprise an optical sensor configured to measure optical reflections from the skin, and/or an ultrasound transducer configured to measure ultrasound reflections from the skin.

Based on the output signal from sensor 32, the controller ascertains the value of at least one parameter. For example, based on output from a temperature sensor, the controller may ascertain the temperature of the skin. Alternatively or additionally, based on output from a current sensor, the controller may ascertain a property, such as the amplitude and/or phase, of the applied current. Alternatively or additionally, based on output from a voltage sensor, the controller may ascertain a property, such as the amplitude and/or phase, of the voltage between the activated electrodes. Alternatively or additionally, based on output from the aforementioned current sensor and/or voltage sensor, the controller may ascertain the impedance of the skin; for example, the controller may divide the voltage amplitude measured by the voltage sensor by the current amplitude measured by the current sensor.

Typically, the parameter values are ascertained periodically, e.g., with a period of between several microseconds and one second.

In response to ascertaining each parameter value, the controller identifies a treatment setting from among multiple treatment settings, by applying at least one decision rule to the ascertained value. For example, the controller may input the parameter value to a machine-learned model such as a decision tree or forest, which is configured to select a treatment setting responsively to the input by implementing a set of decision rules. Alternatively, the decision rules may be represented by a mapping from multiple domains of the parameter to the treatment settings, respectively, such that the controller may identify the treatment setting by identifying the domain to which the value belongs. In other words, as further described below with reference to FIGS. 2-3, the controller may identify the domain to which the ascertained value belongs, and then identify the treatment setting to which, per the mapping, the domain is mapped.

In response to identifying the treatment setting, the controller causes the RF generators to cause one or more RF currents to pass, through the skin, between the electrodes in accordance with the identified treatment setting. In particular, if, when the treatment setting is identified, an RF current is already being applied in accordance with the identified treatment setting, the controller causes the application of this current to continue. (This causation may be active, in that the controller may communicate an appropriate control signal to the RF generators such that the RF generators continue applying the current, or passive, in that the controller may refrain from stopping the RF generators from applying the current.) Otherwise, if an RF current is being applied in accordance with a different treatment setting, the controller stops the application of this current by communicating an appropriate control signal to the RF generators. Subsequently, or if no RF current is being applied when the treatment setting is identified, the controller applies a new RF current in accordance with the identified treatment setting by communicating an appropriate control signal to the RF generators.

Typically, the peak-to-peak amplitude of each RF current is between 20 and 130 V (e.g., between 40 and 55 V). In some embodiments, the RF currents are pulsed, e.g., such that the duration of each RF current—which, in these embodiments, may also be referred to as a "pulse"—is between 1 and 1000 ms. (The amplitude and/or duration of each pulse may be varied, so as to deliver a desired amount of energy to the skin.) Alternatively, a single current may be applied continuously until the next treatment setting is identified, or until the treatment session is terminated.

During or following each treatment session, the controller may modify at least one decision rule in response to the ascertained parameter values. For example, if the decision rules are implemented in a machine-learned model, the controller may retrain the model. Alternatively, as further described below with reference to FIGS. 2-3, the controller may modify the boundary of at least one parameter-value domain stored in memory 34.

Alternatively or additionally to the components described above, device 21 may comprise any other suitable components, such as a power button or switch, a battery configured to power the device, one or more light-emitting diode (LED) indicators, and/or a movement sensor, such as an accelerometer. In response to the movement sensor ceasing to detect movement of the device across the skin, the controller may cause the device to power off, thus protecting the skin of the user from excessive electric current.

In some embodiments, as shown in FIG. 1, a different respective RF generator is connected to each one of the electrodes. (Each RF generator also has a connection to ground, which is not shown in the figure.) In such embodiments, each electric current is typically generated by applying one RF signal to one electrode, and another RF signal with the same amplitude but opposite phase to another electrode. The voltage between the pair may then be ascertained by measuring the voltage at one of the electrodes and multiplying this voltage by two. In other embodiments, a single RF generator is connected to all of the electrodes. As yet another alternative, various sets of multiple electrodes may be connected to different respective RF generators.

In some embodiments, each RF generator operates as a voltage source, in that the RF generator is configured to apply a predetermined voltage. Nonetheless, since the amplitude of the voltage that is actually applied may differ from the predetermined amplitude, e.g., due to the battery that powers the device being depleted, the applied voltage may be measured. Similarly, the applied current may be measured even if the RF generator operates as a current source.

In some embodiments, device 21 further comprises a communication interface, such as a network interface (not shown), a WiFi interface, and/or a Bluetooth interface. Via the communication interface, the controller may communicate with an external processor, such as a processor belonging to the user's smartphone and/or a processor 39 belonging to a cloud server 38. (Optionally, the controller may communicate with processor 39 via the user's smartphone.) At least some of this communication may be exchanged over a suitable computer network 40, such as the Internet.

Typically, server 38 further comprises a network interface 37, such as a network interface controller (NIC). Via network interface 37, processor 39 may communicate with device 21, with the user's smartphone, and/or with any number of other devices belonging to other users.

In general, each of the processors described herein may be embodied as a single processor or as a cooperatively networked or clustered set of processors. In some embodiments, the functionality of at least one of the processors, as described herein, is implemented solely in hardware, e.g., using one or more Application-Specific Integrated Circuits (ASICs) or Field-Programmable Gate Arrays (FPGAs). In other embodiments, the functionality of each processor is implemented at least partly in software. For example, in some embodiments, each processor is embodied as a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Adaptively Treating the Skin

Figure 2:
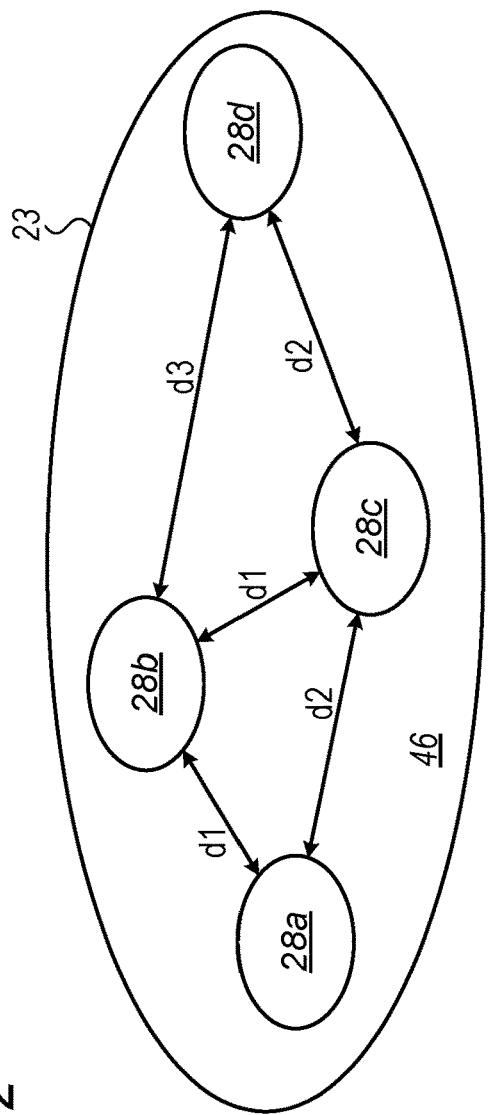
FIGS. 2-3 are schematic illustrations of techniques for treating skin of a user in accordance with various treatment settings, in accordance with some embodiments of the present invention.

Reference is now made to FIG. 2, which is a schematic illustration of a technique for treating skin of a user in accordance with various treatment settings, in accordance with some embodiments of the present invention.

In some embodiments, the skin-tightening device comprises at least three electrodes, at least one pair of the electrodes being spaced farther apart from one another than is another pair of the electrodes. In the particular example embodiment shown in FIG. 2, for example, four electrodes protrude from distal surface 46: a first electrode 28a, a second electrode 28b, a third electrode 28c, and a fourth electrode 28d. Some pairs of these electrodes have a first inter-electrode spacing d1, others have a second inter-electrode spacing d2, which is greater than d1, and another has a third inter-electrode spacing d3, which is greater than d2. (The spacing between first electrode 28a and fourth electrode 28d is not indicated explicitly in the figure.) As another purely illustrative example, first electrode 28a may be at a distance of d3 from each of second electrode 28b and third electrode 28c, second electrode 28b may be at a distance of d1 from third electrode 28c, and fourth electrode 28d may be at a distance of d2 from each of second electrode 28b and third electrode 28c. (Example values for these distances are 2 mm for d1, 3 mm for d2, and 4 mm for d3.) Alternatively, the electrodes may be of any other suitable number, and/or may be arranged in any other suitable configuration.

In such embodiments, the treatment settings stored in memory 34 specify respective groups of the electrodes for activation. For example, the memory may store a mapping from multiple domains of the relevant parameter, such as the impedance or temperature of the skin, to respective groups of the electrodes for activation. In response to identifying the treatment setting for each ascertained parameter value, the controller causes the RF generators to cause one or more electric currents to pass between the group of electrodes specified, by the identified treatment setting, for activation.

Typically, at least some of the treatment settings specify different respective groups for activation. For example, the hypothetical mapping in FIG. 2 includes four different groups of activated electrodes: (i) the domain [x0, x1) is mapped to the group consisting of first electrode 28a, second electrode 28b, and third electrode 28c, (ii) the domain [x1, x2) is mapped to the group consisting of first electrode 28a, third electrode 28c, and fourth electrode 28d, (iii) the domain [x2, x3) is mapped to the group consisting of second electrode 28b and fourth electrode 28d, and (iv) the domains [x3, x4) and [x4, x5) are each mapped to the group consisting of all of the electrodes.

In some embodiments, the treatment settings further specify respective sets of phases, at least some of the treatment settings specifying different respective sets of phases for the same group of electrodes. In response to identifying the treatment setting, the controller causes the RF generators to apply respective RF signals to the group of the electrodes specified by the treatment setting, the RF signals having, respectively, the set of phases specified by the identified treatment setting.

For example, in FIG. 2, although the domains [x3, x4) and [x4, x5) are mapped to the same group of electrodes, these domains are mapped to different respective sets of phases. In particular, for the domain [x3, x4), first electrode 28a and third electrode 28c have a phase of zero, while second electrode 28b and fourth electrode 28d have a phase of 180 degrees. (Thus, in accordance with this treatment setting, the RF signals are applied to the electrodes such that the polarity of first electrode 28a and third electrode 28c is opposite that of second electrode 28b and fourth electrode 28d.) For the domain [x4, x5), on the other hand, first electrode 28a and fourth electrode 28d have a phase of zero, while second electrode 28b and third electrode 28c have a phase of 180 degrees.

Typically, the domains include multiple skin-area domains corresponding to respective skin areas, each of the skin-area domains corresponding to a respective one of the skin areas by virtue of having been defined based on values of the parameter associated with the skin area. For example, one domain may correspond to a cheek, by virtue of having been defined based on parameter values associated with a cheek, such as cheek impedance values. Another domain may correspond to a forehead, by virtue of having been defined based on parameter values associated with a forehead, such as forehead impedance values.

In some embodiments, the parameter values used to define the skin-area domains are collected during a calibration procedure. During this procedure, the user runs the treatment head over the areas of skin for which the skin-area domains are to be defined. For each of these areas, RF currents are applied to the area, while the values of the parameter are ascertained.

For example, prior to using the device for treatment, the user may run the treatment head (with a suitably-thick layer of gel covering the electrodes) over multiple specific skin areas in sequence, indicating to the controller (e.g., by pushing a particular button) each transition from one skin area to the next. For each of the skin areas, the controller may ascertain a plurality of parameter values, and then define the domain for the skin area based on the ascertained values. For example, for each skin area, the controller may compute a respective characteristic value (CV), e.g., by computing the average of the ascertained values (excluding any outliers). The controller may then set the boundaries of the domains such that each boundary between adjacent domains is equidistant from the respective characteristic values of the adjacent domains.

For example, based on the calibration procedure, the controller may compute a characteristic impedance of $Z_C$ for the user's cheek and a characteristic impedance of $Z_F$ for the user's forehead. Responsively thereto, the controller may set a boundary of $(Z_C+Z_F)/2$ between the cheek domain and the forehead domain.

In other embodiments, the values are collected from a suitable population of other users. Based on the values, a processor (e.g., processor 39 (FIG. 1)) defines a set of default skin-area domains, which may be loaded into the memory of each skin-tightening device during the manufacture thereof.

In any case, regardless of whether the domains are computed from a user-specific calibration procedure or from data obtained from the general population, the boundaries of the domains may be adjusted throughout the lifetime of the device, as further described below.

In some embodiments, the domains in memory 34 further include one or more improper-electrical-contact domains corresponding to different respective states in which the electrodes are not in proper electrical contact with the skin. Responsively to ascertaining, during the treatment, a value of the parameter belonging to an improper-electrical-contact domain, the controller ceases treating the skin, or pauses the treatment until proper electrical contact is restored.

Typically, at least one of the improper-electrical-contact domains corresponds to a state in which the electrodes are not in any electrical contact with the skin. For example, a "gel domain," which may include, for example, impedances between 550 and 800Ω, may correspond to a state in which the electrodes are covered by a layer of gel having a thickness within the predefined range, but are not in electrical contact with the skin. As another example, an "air domain," which may include, for example, impedances higher than 4000Ω, may correspond to a state in which the electrodes are not covered by gel and are not in electrical contact with the skin. As another example, a "short-circuit domain," which may include, for example, impedances less than 100Ω, may correspond to a state in which the electrodes are electrically connected to each other via a low-resistance conductor, such as the user's wristwatch.

Alternatively or additionally, one of the improper-electrical-contact domains may correspond to a state in which the electrodes are in electrical contact with the skin but not via a layer of gel having a thickness within the predefined range; in other words, the electrodes may be covered by too little or too much gel. As a purely illustrative example, a domain corresponding to skin contact with too little intervening gel may include impedances between 1800 and 4000Ω, while a domain corresponding to skin contact with too much intervening gel may include impedances between 100 and 200Ω.

In some embodiments, responsively to identifying a state in which the electrodes are not in proper electrical contact with the skin, the controller generates an output indicating the state. For example, in response to identifying an improper amount of gel, the controller may cause an appropriate LED indicator to be lit, such that the user realizes the need to increase or decrease the amount of gel. Alternatively or additionally, the controller may communicate a message indicating the state to an external device, such as server 38 (FIG. 1) or the user's smartphone. Responsively to receiving this message, the external device may generate an output to the user indicating the state, along with any action required to resume treatment. For example, in the case of an improper amount of gel, the user may be instructed to increase or decrease the amount of gel.

Each of the improper-electrical-contact domains may be defined by passing RF currents between the electrodes, and ascertaining values of the relevant parameter, while the electrodes are in the associated state of improper electrical contact. Alternatively, at least one of the improper-electrical-contact domains may be defined based on preexisting data, such as tables of impedance values for different types of materials. In any case, typically, the same set of improper-electrical-contact domains is loaded into the memory of each skin-tightening device during the manufacture thereof.

During each treatment session, the controller may store, in memory 34, each ascertained value belonging to each domain. Subsequently, following the treatment session, based on the stored values, the controller may modify the respective characteristic values of one or more of the domains. The controller may then reset at least one of the domain boundaries responsively to the modified characteristic values. For example, the controller may set each boundary to be equidistant from the two nearest characteristic values.

In some embodiments, the controller modifies the characteristic value of a domain by computing the mean of the ascertained values belonging to the domain and then setting the characteristic value to a weighted average of the (current) characteristic value and the mean. In other words, given a characteristic value $CV_i$ and a mean M of the ascertained values, the controller may compute a new characteristic value $CV_{i+1}$ as $\alpha CV_{i+}(1-\alpha)M$, where a is a suitable constant between zero and one, such as a constant between 0.3 and 0.99, e.g., between 0.85 and 0.95.

Alternatively to assigning a single characteristic value to each domain, the controller may assign multiple characteristic values to each domain, e.g., by computing several local averages of a plurality of parameter values belonging to the domain. In such embodiments, responsively to a plurality of parameter values ascertained during a treatment session, the controller may update one or more of the local averages. Subsequently, the controller may modify the boundary between two adjacent domains by minimizing the sum of squared distances between the boundary and the local averages in the adjacent domains, or using any other suitable technique.

Figure 3:
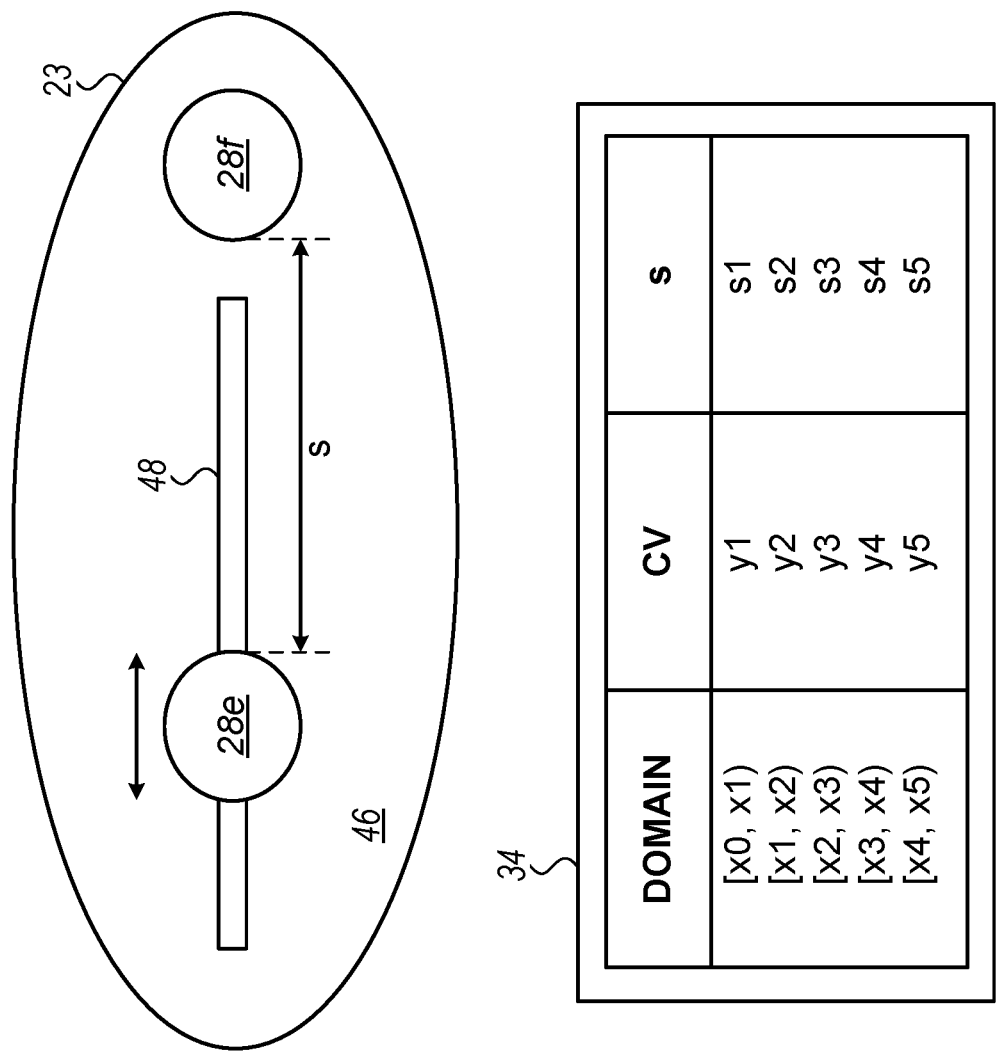

Reference is now made to FIG. 3, which is a schematic illustration of another technique for treating skin of a user in accordance with various treatment settings, in accordance with some embodiments of the present invention.

In some embodiments, surface 46 is shaped to define a track 48, and at least one electrode 28e is moveable along track 48, such that the inter-electrode separation "s" between electrode 28e and another electrode 28f is adjustable. For example, the moveable electrode may be situated within the track, with the proximal end of the moveable electrode, which lies beneath surface 46, threaded onto a screw lying parallel to the track and coupled to a motor. By using the motor to turn the screw, controller may move the moveable electrode along the track, toward or away from electrode 28f.

In such embodiments, at least some of the treatment settings stored in memory 34 specify different respective inter-electrode separations. For example, FIG. 3 shows, for the same set of hypothetical domains shown in FIG. 2, different respective inter-electrode separations s1, s2, s3, s4, and s5. During the treatment session, in response to identifying the appropriate treatment setting, the controller moves electrode 28e along the track such that electrode 28e and electrode 28f are spaced apart from one another by the inter-electrode separation specified by the treatment setting. Subsequently to moving electrode 28e, the controller causes the RF generators to cause one or more electric currents to pass between electrode 28e and electrode 28f. (It is noted that a treatment setting may specify an inter-electrode separation implicitly, by specifying the position of the moveable electrode with respect to any coordinate system.)

In general, for such embodiments, the controller may modify the characteristic values and/or the boundaries for the domains as described above with reference to FIG. 2.

In some embodiments, treatment head 23 comprises one or more pairs of fixed-location electrodes, as in FIG. 2, together with at least one moveable electrode, as in FIG. 3. A treatment setting may thus specify a group of activated electrodes (along with, optionally, respective phases for the group), together with an inter-electrode separation for the moveable electrode.

It is noted that the treatment settings may specify additional treatment parameters not described above with reference to FIGS. 2-3. For example, two treatment settings may specify different respective voltage or current amplitudes.

In some cases, a combination of domains may be mapped to a single treatment setting. Thus, for example, a particular domain of impedance values in combination with a first domain of temperature or moistness values may be mapped to a first treatment setting, while the same domain of impedance values in combination with a second domain of temperature or moistness values may be mapped to a second treatment setting.

Advantageously, combining an impedance domain with a temperature or moistness domain may account for the fact that the impedance of skin may be a function of the temperature or moistness of the skin, such that a single impedance domain may correspond to different respective areas of skin at different respective temperatures or levels of moistness. Furthermore, this scheme may facilitate providing multiple treatment settings for a single skin area. For example, at the beginning of a treatment session, when the skin temperature is relatively low, a first treatment setting, specifying a relatively large number of activated electrodes, may be used. As the session continues and the skin temperature approaches a predefined safety threshold, however, a second treatment setting, specifying fewer activated electrodes, may be used.

Example Algorithms

Figure 4A:
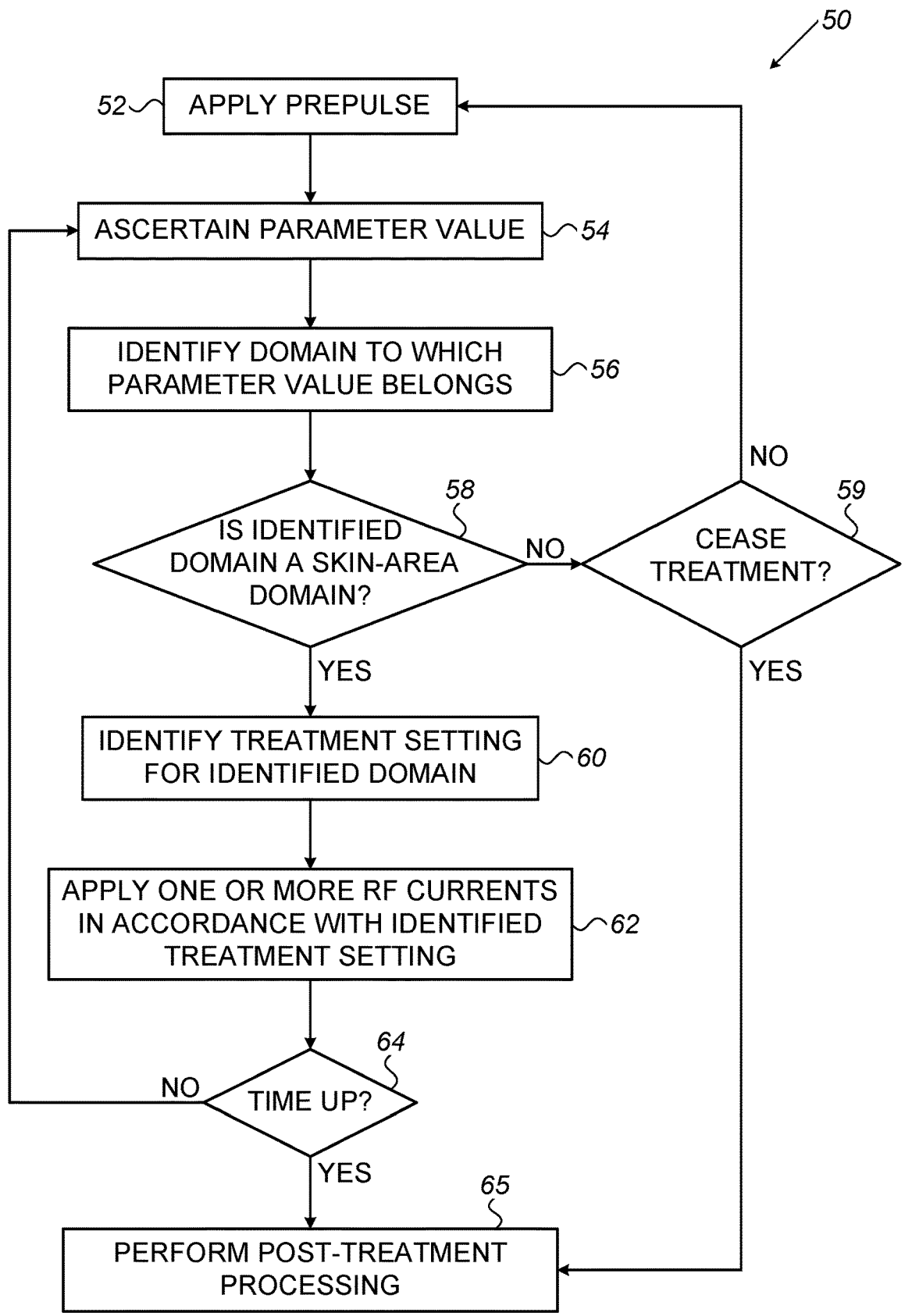
FIG. 4A is a flow diagram for an iterative method for treating skin, in accordance with some embodiments of the present invention.

Reference is now made to FIG. 4A, which is a flow diagram for an iterative method 50 for treating skin, in accordance with some embodiments of the present invention. Method 50 is executed by controller 36 (FIG. 1) following the powering-on of device 21 (FIG. 1), and, optionally, an input from the user (e.g., via the pressing of an appropriate button) indicating that the user wishes to begin a treatment session.

Typically, method 50 begins with a prepulse-applying step 52, at which the controller, prior to treating the skin, causes the RF generators to cause a pre-treatment electric current to pass, through the skin, between any pair of the electrodes. (The duration of this "prepulse" is typically between 1 and 20 ms, e.g., between 1 and 5 ms.) In some embodiments, a single pair of electrodes on the treatment head is designated for application of the prepulse; in other embodiments, the pair used for the prepulse may vary from one application to the next.

Based on the prepulse, the controller ascertains an initial value of the relevant parameter, such as the temperature of the skin, the amplitude and/or phase of the prepulse, or the amplitude and/or phase of the inter-electrode voltage, at a parameter-value-ascertaining step 54. Subsequently, at a domain-identifying step 56, the controller identifies the domain to which the parameter value belongs.

Next, at a domain-classifying step 58, the controller checks whether the identified domain is a skin-area domain. If yes, the controller, at a setting-identifying step 60, identifies the treatment setting to which, per the mapping in memory 34 (FIG. 1), the identified domain is mapped. In response to identifying the treatment setting, the controller, at a current-applying step 62, causes the RF generators to cause one or more electric currents to pass, through the skin, between the electrodes in accordance with the identified treatment setting.

On the other hand, if the identified domain is not a skin-area domain (but rather, is an improper-electrical-contact domain), the controller decides, at a deciding step 59, whether to cease treatment of the skin. For example, the controller may ascertain whether the identified domain corresponds to a state in which the device or the user is at risk of being harmed, such as in the case of a short circuit or of the electrodes being covered by an insufficient amount of gel. If the controller decides to cease treatment, the controller proceeds to a post-treatment processing step 65, described below. Otherwise, the controller returns to prepulse-applying step 52. The controller may thus apply repeated prepulses until proper electrical contact is established between the electrodes and the skin.

Following current-applying step 62, the controller, at a duration-checking step 64, checks whether the duration of the treatment session thus far exceeds a predefined safety limit, such as two or three minutes. If not, the controller returns to parameter-value-ascertaining step 54. Otherwise, the controller ceases to treat the skin, and proceeds to post-treatment processing step 65. Similarly, as described above with reference to FIG. 1, the treatment may be stopped in response to a lack of detected motion of the device. Likewise, the treatment may be stopped in response to the temperature of the skin exceeding the aforementioned predefined safety threshold, or in response to the user actively terminating the treatment, e.g., by pressing an appropriate button.

Figure 4B:
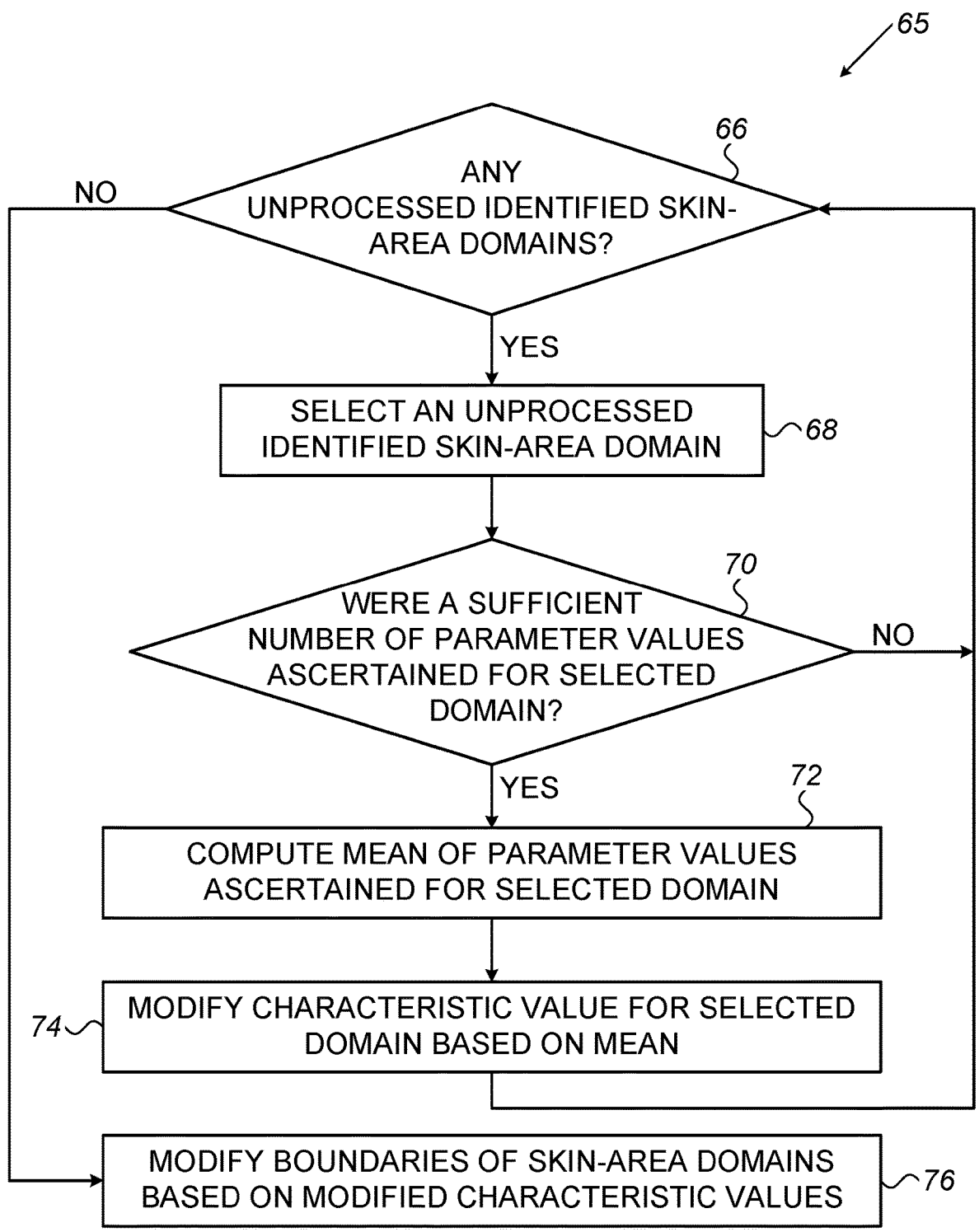
FIG. 4B is a flow diagram for post-treatment processing, in accordance with some embodiments of the present invention.

Following the treatment of the skin, the controller performs post-treatment processing step 65, in which the controller, typically using artificial intelligence, modifies at least one boundary of at least one of the parameter-value domains in response to the parameter values ascertained during the treatment. In this regard, reference is now made to FIG. 4B, which is a flow diagram for post-treatment processing step 65, in accordance with some embodiments of the present invention.

Post-treatment processing step 65 begins with a first checking step 66, at which the controller checks whether any of the skin-area domains identified during the performance of method 50 were not yet processed. If yes, the controller selects an unprocessed identified skin-area domain, at a domain-selecting step 68. Subsequently, at a second checking step 70, the controller checks whether the number of parameter values ascertained for the selected domain exceeds a predefined threshold. If yes, the controller, at a mean-computing step 72, computes the mean of the parameter values ascertained for the selected domain (excluding any outliers). Subsequently, at a characteristic-value-modifying step 74, the controller modifies the characteristic value for the selected domain, based on the mean. For example, as described above with reference to FIG. 2, the controller may compute a weighted average of the characteristic value and the mean. Subsequently to characteristic-value-modifying step 74, or if not enough parameter values were ascertained, the controller returns to first checking step 66.

In response to ascertaining, at first checking step 66, that no unprocessed identified skin-area domains remain, the controller, at a boundary-modifying step 76, modifies the boundaries of the skin-area domains based on the modified characteristic values. For example, as described above with reference to FIG. 2, the controller may set each boundary of each skin-area domain to be midway between the characteristic value of the domain and the characteristic value of the relevant adjacent domain.

Other Embodiments

In some embodiments, server 38 (FIG. 1) and controller 36 are configured to cooperatively carry out a process that includes comparing a quantity derived from at least some of the ascertained parameter values to a baseline quantity, and responsively to the comparing, generating an output to the user, e.g., by sending an email message to the user's email account or a text message to the user's phone.

For example, the controller may communicate multiple ascertained values of the temperature or impedance of at least one area of the user's skin to the server. The server may then compute the mean or median of these values, and compare this quantity to a baseline. (Alternatively, the controller may compute the mean or median, and communicate this quantity to server.) In response to the comparison, the server may ascertain an attribute of the skin, such as the moistness of the skin. Responsively thereto, the server may generate an output to the user, such as a message indicating the attribute (e.g., a message indicating that the skin is dry) and/or a recommendation for a skin-care product (e.g., a moisturizer). Recommendations for skin-care products may also be issued to the user irrespective of the properties of the user's skin, based on data collected from other users.

Alternatively or additionally, the controller and at least one external processor, such as processor 39 (FIG. 1) belonging to server 38 and/or a processor belonging to the user's smartphone, may cooperatively perform at least some of the functionality described above with reference to the figures. For example, during each treatment session, the controller may communicate each ascertained parameter value to the external processor, and the external processor may then identify the appropriate treatment setting and communicate the treatment setting to the controller. Alternatively or additionally, the post-treatment processing, in which the decision rules are modified, may be performed by the external processor.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system, comprising:
a plurality of electrodes;
one or more radiofrequency (RF) generators; and
a controller, configured to:
using one or more decision rules, treat skin of a user responsively to multiple ascertained values of at least one parameter, by iteratively:
ascertaining at least one respective value of the ascertained values,
by applying at least one of the decision rules to the ascertained value, identifying a treatment setting from among multiple treatment settings, and
causing the one or more RF generators to cause one or more RF currents to pass, through the skin, between at least some of the electrodes in accordance with the identified treatment setting, and
modify at least one of the decision rules in response to the ascertained values,
wherein the decision rules are represented by a mapping from multiple domains of the parameter, which are associated with different respective characteristic values, to the treatment settings, respectively,
wherein the controller is configured to identify the treatment setting by identifying the domain to which the ascertained value belongs, and
wherein the controller is configured to modify the at least one of the decision rules by modifying at least one boundary of at least one of the domains, by:
modifying the characteristic value of the at least one of the domains, based on those of the ascertained values belonging to the at least one of the domains, and
setting the boundary responsively to the modified characteristic value of the at least one of the domains.

2. The system according to claim 1, wherein the system comprises multiple RF generators, and wherein a different respective one of the RF generators is connected to each one of the electrodes.

3. The system according to claim 1,
wherein the electrodes comprise at least three electrodes, at least one pair of the electrodes being spaced farther apart from one another than is another pair of the electrodes,
wherein the treatment settings specify respective groups of the electrodes for activation, and
wherein the controller is configured to cause the one or more RF generators to cause the RF currents to pass between the group of the electrodes specified, for activation, by the identified treatment setting.

4. The system according to claim 3, wherein at least some of the treatment settings specify, for activation, different respective ones of the groups.

5. The system according to claim 3,
wherein the treatment settings further specify respective sets of phases, at least some of the treatment settings specifying different respective ones of the sets for the same one of the groups, and wherein the controller is configured to cause the one or more RF generators to cause the RF currents to pass between the group of the electrodes by causing the one or more RF generators to apply respective RF signals to the group of the electrodes, the RF signals having, respectively, the set of phases specified by the identified treatment setting.

6. The system according to claim 1, further comprising a surface shaped to define a track, wherein at least one of the electrodes is moveable along the track, wherein at least some of the treatment settings specify different respective inter-electrode separations, and wherein the controller is configured to cause the one or more RF generators to cause the RF currents to pass between the at least some of the electrodes in accordance with the identified treatment setting by:

moving the moveable electrode along the track such that the moveable electrode and another one of the electrodes are spaced apart from one another by the inter-electrode separation specified by the identified treatment setting, and subsequently to moving the moveable electrode, causing the one or more RF generators to cause the RF currents to pass between the moveable electrode and the other one of the electrodes.

7. The system according to claim 1, wherein the controller is configured to set the boundary to be equidistant from (i) the modified characteristic value of the at least one of the domains, and (ii) the characteristic value of another one of the domains that is adjacent to the at least one of the domains.

8. The system according to claim 1, wherein the controller is configured to modify the characteristic value of the at least one of the domains by:

computing a mean of those of the ascertained values belonging to the at least one of the domains, and setting the characteristic value to a weighted average of (i) the characteristic value, and (ii) the mean.

9. The system according to claim 1, wherein the ascertained values are first ascertained values, and wherein the domains include multiple skin-area domains corresponding to respective skin areas, each of the skin-area domains corresponding to a respective one of the skin areas by virtue of having been defined based on second ascertained values of the parameter associated with the skin area.

10. The system according to claim 1, further comprising a temperature sensor configured to measure a temperature of the skin and to generate a temperature-sensor output responsively thereto, wherein the ascertained values include temperature-values of the temperature, and wherein the controller is configured to ascertain the temperature-values responsively to the temperature-sensor output.

11. The system according to claim 1, further comprising an electric-current sensor configured to measure at least some of the RF currents and to generate an output responsively thereto, wherein the controller is configured to ascertain the ascertained values responsively to the output.

12. The system according to claim 11, wherein the ascertained values include electric-current-property-values of a property of the at least some of the RF currents.

13. The system according to claim 1, further comprising a voltage sensor configured to measure a voltage associated with at least some of the RF currents and to generate a voltage-sensor output responsively thereto, wherein the controller is configured to ascertain the ascertained values responsively to the voltage-sensor output.

14. The system according to claim 13, wherein the ascertained values include voltage-property-values of a property of the voltage.

15. The system according to claim 1, wherein the ascertained values include impedance-values of an impedance of the skin.

16. The system according to claim 1, wherein the controller is further configured to cause the one or more RF generators, prior to treating the skin, to cause a pre-treatment electric current to pass, through the skin, between any pair of the electrodes, and wherein the controller is configured to ascertain an initial one of the ascertained values based on the pre-treatment electric current.

17. The system according to claim 1, further comprising a server configured to communicate with the controller over a computer network, wherein the server and the controller are configured to cooperatively carry out a process that includes:

comparing a quantity derived from the ascertained values to a baseline quantity, and responsively to the comparing, generating an output to the user.

18. A system, comprising:

a plurality of electrodes;

one or more radiofrequency (RF) generators; and a controller, configured to:

using one or more decision rules, treat skin of a user responsively to multiple first ascertained values of at least one parameter, by iteratively:

ascertaining at least one respective value of the ascertained values, by applying at least one of the decision rules to the ascertained value, identifying a treatment setting from among multiple treatment settings, and causing the one or more RF generators to cause one or more RF currents to pass, through the skin, between at least some of the electrodes in accordance with the identified treatment setting, and modify at least one of the decision rules in response to the ascertained values, wherein the decision rules are represented by a mapping from multiple domains of the parameter to the treatment settings, respectively, wherein the controller is configured to identify the treatment setting by identifying the domain to which the ascertained value belongs, wherein the controller is configured to modify the at least one of the decision rules by modifying at least one boundary of at least one of the domains, wherein the domains include multiple skin-area domains corresponding to respective skin areas, each of the skin-area domains corresponding to a respective one of the skin areas by virtue of having been defined based on second ascertained values of the parameter associated with the skin area, and wherein the skin areas include a cheek and a forehead.

19. A system, comprising:
a plurality of electrodes;
one or more radiofrequency (RF) generators; and
a controller, configured to:
  using one or more decision rules, treat skin of a user responsively to multiple first ascertained values of at least one parameter, by iteratively:
    ascertaining at least one respective value of the ascertained values,
    by applying at least one of the decision rules to the ascertained value, identifying a treatment setting from among multiple treatment settings, and
    causing the one or more RF generators to cause one or more RF currents to pass, through the skin, between at least some of the electrodes in accordance with the identified treatment setting, and
  modify at least one of the decision rules in response to the ascertained values,
wherein the decision rules are represented by a mapping from multiple domains of the parameter to the treatment settings, respectively,
wherein the controller is configured to identify the treatment setting by identifying the domain to which the ascertained value belongs,
wherein the controller is configured to modify the at least one of the decision rules by modifying at least one boundary of at least one of the domains,
wherein the domains include multiple skin-area domains corresponding to respective skin areas,
  each of the skin-area domains corresponding to a respective one of the skin areas by virtue of having been defined based on second ascertained values of the parameter associated with the skin area,
wherein the domains further include one or more improper-electrical-contact domains corresponding to different respective states in which the electrodes are not in proper electrical contact with the skin, and
wherein the controller is further configured to:
  ascertain another value of the parameter,
  ascertain that the other value belongs to one of the improper-electrical-contact domains, and
  cease treating the skin, responsively to ascertaining that the other value belongs to the improper-electrical-contact domain.

20. The system according to claim 19, wherein the states include a state in which the electrodes are not in any electrical contact with the skin.

21. The system according to claim 19, wherein the states include a state in which the electrodes are in electrical contact with the skin but not via a layer of gel having a thickness within a predefined range.

22. The system according to claim 19, wherein the controller is further configured to generate an output indicating the state to which the improper-electrical-contact domain corresponds.

23. A system, comprising:
a plurality of electrodes;
one or more radiofrequency (RF) generators;
a controller, configured to:
  using one or more decision rules, treat skin of a user responsively to multiple ascertained values of at least one parameter, by iteratively:
    ascertaining at least one respective value of the ascertained values,
    by applying at least one of the decision rules to the ascertained value, identifying a treatment setting from among multiple treatment settings, and
    causing the one or more RF generators to cause one or more RF currents to pass, through the skin, between at least some of the electrodes in accordance with the identified treatment setting, and
  modify at least one of the decision rules in response to the ascertained values; and
a server configured to communicate with the controller over a computer network,
wherein the server and the controller are configured to cooperatively carry out a process that includes:
  comparing a quantity derived from the ascertained values to a baseline quantity, and
  responsively to the comparing, generating an output to the user, and wherein the output includes a message indicating an attribute of the skin.

24. The system according to claim 23,
wherein the decision rules are represented by a mapping from multiple domains of the parameter to the treatment settings, respectively,
wherein the controller is configured to identify the treatment setting by identifying the domain to which the ascertained value belongs, and
wherein the controller is configured to modify the at least one of the decision rules by modifying at least one boundary of at least one of the domains.

25. The system according to claim 24,
wherein the domains are associated with different respective characteristic values, and
wherein the controller is configured to modify the boundary of the at least one of the domains by:
  modifying the characteristic value of the at least one of the domains, based on those of the ascertained values belonging to the at least one of the domains, and
  setting the boundary responsively to the modified characteristic value of the at least one of the domains.

26. A system, comprising:
a plurality of electrodes;
one or more radiofrequency (RF) generators;
a controller, configured to:
  using one or more decision rules, treat skin of a user responsively to multiple ascertained values of at least one parameter, by iteratively:
    ascertaining at least one respective value of the ascertained values,
    by applying at least one of the decision rules to the ascertained value, identifying a treatment setting from among multiple treatment settings, and
    causing the one or more RF generators to cause one or more RF currents to pass, through the skin, between at least some of the electrodes in accordance with the identified treatment setting, and
  modify at least one of the decision rules in response to the ascertained values; and
a server configured to communicate with the controller over a computer network,
wherein the server and the controller are configured to cooperatively carry out a process that includes:
  comparing a quantity derived from the ascertained values to a baseline quantity, and
  responsively to the comparing, generating an output to the user, and
wherein the output includes a recommendation for a skin-care product.

27. A method, comprising:
using one or more decision rules, treating skin of a user responsively to multiple ascertained values of at least one parameter, by iteratively:

ascertaining at least one respective value of the ascertained values, by applying at least one of the decision rules to the ascertained value, identifying a treatment setting from among multiple treatment settings, and causing one or more radiofrequency (RF) currents to pass, through the skin, between at least some of a plurality of electrodes in accordance with the identified treatment setting; and modifying at least one of the decision rules in response to the ascertained values, wherein the decision rules are represented by a mapping from multiple domains of the parameter to the treatment settings, respectively, wherein identifying the treatment setting comprises identifying the treatment setting by identifying the domain to which the ascertained value belongs, wherein modifying the at least one of the decision rules comprises modifying the at least one of the decision rules by modifying at least one boundary of at least one of the domains, wherein the domains are associated with different respective characteristic values, and wherein modifying the boundary of the at least one of the domains comprises:
    modifying the characteristic value of the at least one of the domains, based on those of the ascertained values belonging to the at least one of the domains; and
    setting the boundary responsively to the modified characteristic value of the at least one of the domains.

28. The method according to claim 27,
wherein the electrodes comprise at least three electrodes, at least one pair of the electrodes being spaced farther apart from one another than is another pair of the electrodes,
wherein the treatment settings specify respective groups of the electrodes for activation, and
wherein causing the RF currents to pass between the at least some of the electrodes comprises causing the RF currents to pass between the group of the electrodes specified, for activation, by the identified treatment setting.

29. The method according to claim 28, wherein at least some of the treatment settings specify, for activation, different respective ones of the groups.

30. The method according to claim 28,
wherein the treatment settings further specify respective sets of phases, at least some of the treatment settings specifying different respective ones of the sets for the same one of the groups, and
wherein causing the RF currents to pass between the group of the electrodes comprises causing the RF currents to pass between the group of the electrodes by causing one or more RF generators to apply respective RF signals to the group of the electrodes, the RF signals having, respectively, the set of phases specified by the identified treatment setting.

31. The method according to claim 27,
wherein at least one of the electrodes is moveable along a track,
wherein at least some of the treatment settings specify different respective inter-electrode separations, and
wherein causing the RF currents to pass between the at least some of the electrodes in accordance with the identified treatment setting comprises:
    moving the moveable electrode along the track such that the moveable electrode and another one of the electrodes are spaced apart from one another by the inter-electrode separation specified by the identified treatment setting; and
    subsequently to moving the moveable electrode, causing the RF currents to pass between the moveable electrode and the other one of the electrodes.

32. The method according to claim 27, wherein setting the boundary comprises setting the boundary to be equidistant from (i) the modified characteristic value of the at least one of the domains, and (ii) the characteristic value of another one of the domains that is adjacent to the at least one of the domains.

33. The method according to claim 27, wherein modifying the characteristic value comprises:
    computing a mean of those of the ascertained values belonging to the at least one of the domains; and
    setting the characteristic value to a weighted average of (i) the characteristic value, and (ii) the mean.

34. The method according to claim 27,
wherein the ascertained values are first ascertained values, and
wherein the domains include multiple skin-area domains corresponding to respective skin areas,
    each of the skin-area domains corresponding to a respective one of the skin areas by virtue of having been defined based on second ascertained values of the parameter associated with the skin area.

35. The method according to claim 27, wherein the ascertained values include temperature-values of a temperature of the skin.

36. The method according to claim 27, further comprising measuring at least some of the RF currents and generating an output responsively thereto, wherein the method comprises ascertaining the ascertained values responsively to the output.

37. The method according to claim 36, wherein the ascertained values include electric-current-property-values of a property of the at least some of the RF currents.

38. The method according to claim 27, further comprising measuring a voltage associated with at least some of the RF currents and generating a voltage-indicating output responsively thereto, wherein the method comprises ascertaining the ascertained values responsively to the voltage-indicating output.

39. The method according to claim 38, wherein the ascertained values include voltage-property-values of a property of the voltage.

40. The method according to claim 27, wherein the ascertained values include impedance-values of an impedance of the skin.

41. The method according to claim 27, further comprising, prior to treating the skin, causing a pre-treatment electric current to pass, through the skin, between any pair of the electrodes,
    wherein the method comprises ascertaining an initial one of the ascertained values based on the pre-treatment electric current.

42. The method according to claim 27, further comprising:
    comparing a quantity derived from the ascertained values to a baseline quantity; and
    responsively to the comparing, generating an output to the user.

43. A method, comprising:
    using one or more decision rules, treating skin of a user responsively to multiple first ascertained values of at least one parameter, by iteratively:

ascertaining at least one respective value of the ascertained values,
by applying at least one of the decision rules to the ascertained value, identifying a treatment setting from among multiple treatment settings, and
causing one or more radiofrequency (RF) currents to pass, through the skin, between at least some of a plurality of electrodes in accordance with the identified treatment setting; and
modifying at least one of the decision rules in response to the ascertained values,
wherein the decision rules are represented by a mapping from multiple domains of the parameter to the treatment settings, respectively,
wherein identifying the treatment setting comprises identifying the treatment setting by identifying the domain to which the ascertained value belongs,
wherein modifying the at least one of the decision rules comprises modifying the at least one of the decision rules by modifying at least one boundary of at least one of the domains,
wherein the domains include multiple skin-area domains corresponding to respective skin areas,
each of the skin-area domains corresponding to a respective one of the skin areas by virtue of having been defined based on second ascertained values of the parameter associated with the skin area, and
wherein the skin areas include a cheek and a forehead.

44. A method, comprising:
using one or more decision rules, treating skin of a user responsively to multiple first ascertained values of at least one parameter, by iteratively:
ascertaining at least one respective value of the ascertained values,
by applying at least one of the decision rules to the ascertained value, identifying a treatment setting from among multiple treatment settings, and
causing one or more radiofrequency (RF) currents to pass, through the skin, between at least some of a plurality of electrodes in accordance with the identified treatment setting; and
modifying at least one of the decision rules in response to the ascertained values,
wherein the domains include multiple skin-area domains corresponding to respective skin areas,
each of the skin-area domains corresponding to a respective one of the skin areas by virtue of having been defined based on second ascertained values of the parameter associated with the skin area,
wherein the domains further include one or more improper-electrical-contact domains corresponding to different respective states in which the electrodes are not in proper electrical contact with the skin, and
wherein the method further comprises:
ascertaining another value of the parameter;
ascertaining that the other value belongs to one of the improper-electrical-contact domains; and
ceasing to treat the skin, responsively to ascertaining that the other value belongs to the improper-electrical-contact domain.

45. The method according to claim 44, wherein the states include a state in which the electrodes are not in any electrical contact with the skin.

46. The method according to claim 44, wherein the states include a state in which the electrodes are in electrical contact with the skin but not via a layer of gel having a thickness within a predefined range.

47. The method according to claim 44, further comprising generating an output indicating the state to which the improper-electrical-contact domain corresponds.

48. A method, comprising:
using one or more decision rules, treating skin of a user responsively to multiple ascertained values of at least one parameter, by iteratively:
ascertaining at least one respective value of the ascertained values,
by applying at least one of the decision rules to the ascertained value, identifying a treatment setting from among multiple treatment settings, and
causing one or more radiofrequency (RF) currents to pass, through the skin, between at least some of a plurality of electrodes in accordance with the identified treatment setting;
modifying at least one of the decision rules in response to the ascertained values;
comparing a quantity derived from the ascertained values to a baseline quantity; and
responsively to the comparing, generating an output to the user,
wherein the output includes a message indicating an attribute of the skin.

49. The method according to claim 48,
wherein the decision rules are represented by a mapping from multiple domains of the parameter to the treatment settings, respectively,
wherein identifying the treatment setting comprises identifying the treatment setting by identifying the domain to which the ascertained value belongs, and
wherein modifying the at least one of the decision rules comprises modifying the at least one of the decision rules by modifying at least one boundary of at least one of the domains.

50. The method according to claim 49,
wherein the domains are associated with different respective characteristic values, and
wherein modifying the boundary of the at least one of the domains comprises:
modifying the characteristic value of the at least one of the domains, based on those of the ascertained values belonging to the at least one of the domains; and
setting the boundary responsively to the modified characteristic value of the at least one of the domains.

51. A method, comprising:
using one or more decision rules, treating skin of a user responsively to multiple ascertained values of at least one parameter, by iteratively:
ascertaining at least one respective value of the ascertained values,
by applying at least one of the decision rules to the ascertained value, identifying a treatment setting from among multiple treatment settings, and
causing one or more radiofrequency (RF) currents to pass, through the skin, between at least some of a plurality of electrodes in accordance with the identified treatment setting;
modifying at least one of the decision rules in response to the ascertained values;

comparing a quantity derived from the ascertained values to a baseline quantity; and
responsively to the comparing, generating an output to the user,
wherein the output includes a recommendation for a skin-care product.

* * * * *